US009234164B2

(12) United States Patent
Robinson

(10) Patent No.: US 9,234,164 B2

(45) Date of Patent: Jan. 12, 2016

(54) GRAFFITI REMOVER COMPRISING A SOLVENT MIXTURE OF PROPYLENE CARBONATE AND SOY METHYL ESTER

(71) Applicant: Gregory E Robinson, Tonawanda, NY (US)

(72) Inventor: Gregory E Robinson, Tonawanda, NY (US)

( * ) Notice: Subject to any disclaimer, the term of this patent is extended or adjusted under 35 U.S.C. 154(b) by 0 days.

(21) Appl. No.: 14/619,864

(22) Filed: Feb. 11, 2015

(65) Prior Publication Data

US 2015/0225675 A1 Aug. 13, 2015

Related U.S. Application Data

(60) Provisional application No. 61/938,448, filed on Feb. 11, 2014.

(51) Int. Cl.

| | |
|---|---|
| ***C11D 7/44*** | (2006.01) |
| ***C11D 7/26*** | (2006.01) |
| ***C11D 3/43*** | (2006.01) |
| ***C11D 1/72*** | (2006.01) |
| ***C11D 1/825*** | (2006.01) |
| ***C11D 3/382*** | (2006.01) |
| ***C11D 1/66*** | (2006.01) |
| ***C11D 3/20*** | (2006.01) |

(52) U.S. Cl.

CPC .. *C11D 3/43* (2013.01); *C11D 1/66* (2013.01); *C11D 3/2093* (2013.01)

(58) Field of Classification Search

IPC ............ C11D 7/5077,7/44, 7/267, 7/266, 7/26, C11D 3/43, 1/72, 1/825, 3/2093, 3/2096, C11D 3/382

See application file for complete search history.

(56) References Cited

U.S. PATENT DOCUMENTS

| | | | | |
|---|---|---|---|---|
| 5,536,439 | A | 7/1996 | Harbin | |
| 5,990,062 | A | 11/1999 | Summerfield et al. | |
| 6,517,626 | B2 | 2/2003 | Saquet et al. | |
| 6,824,623 | B1 | 11/2004 | Gross et al. | |
| 2003/0119686 | A1 * | 6/2003 | Machac et al. | 510/201 |
| 2011/0041837 | A1 | 2/2011 | Kato et al. | |
| 2011/0265830 | A1 * | 11/2011 | Gonzalez | 134/26 |
| 2014/0311384 | A1 * | 10/2014 | Ledford et al. | 106/311 |

* cited by examiner

*Primary Examiner* — Charles Boyer

(74) *Attorney, Agent, or Firm* — Vincent G. LoTempio; Kloss, Stenger & LoTempio; David Stephenson

(57) ABSTRACT

Provided is a liquid lacquer, acrylic and permanent marker remover that is particularly effective for graffiti removal. The remover is effective on marker graffiti, which is common in areas such as public restrooms, educational institutions, traffic direction devices, public transit vehicles and stations. The remover is also effective on fresh and semi-dry paint. Existing products for this purpose are relatively ineffective and generally toxic. These problems are addressed by providing an effective, environmentally benign, graffiti remover.

3 Claims, No Drawings

GRAFFITI REMOVER COMPRISING A SOLVENT MIXTURE OF PROPYLENE CARBONATE AND SOY METHYL ESTER

FIELD OF THE INVENTION

The present disclosure relates to removing graffiti or other unwanted substances from surfaces, in particular removing graffiti from public areas without harming users of the removal solution, the surfaces cleaned, or the environment.

BACKGROUND OF THE INVENTION

Strong solvents are required to remove permanent marker, lacquers and acrylics from surfaces including walls, bathroom stalls, or vehicle bodies as the lacquer, acrylic and other high VOC solvents must be solubilized before removal. The most common solvent systems used to remove lacquers from walls are acetone, methylene chloride, N-Methyl-2-Pyrrolidone, diethylene glycol monoethyl ether and ethyl acetate, methyl ethyl ketone, acetonitrile, and butyl acetate. These solvents have undesirable properties such as volatility, flammability, toxicity, and strong odor. The use of these types of toxic chemicals in graffiti removers is exemplified in the related art, including U.S. Pat. No. 7,337,788 and WO Patent Application No. 2,011,041,837.

Toxic chemicals of the variety used in lacquer, acrylic and permanent marker removers have been found in fresh water such as ponds, lakes, and streams in high levels. Aquatic organisms, including both plants and animals, are at risk from exposure to high levels of these chemicals in water systems. Further, humans exposed to these chemicals through water systems may suffer from health problems. Additionally, many strong solvents contain toxic or carcinogenic chemicals, including volatile organic compounds (VOCs) and hazardous air pollutants (HAPs) that can pollute the air.

The undesirable and unsafe properties of existing graffiti removers limit their use in public places like schools and bus stations, where people might be exposed during application. While patents have been granted for low toxicity lacquer removers, such as U.S. Pat. No. 5,990,062, attempts to develop alternative formulations for removing graffiti by reducing or eliminating undesirable solvents have met with limited success.

Accordingly, there is a need for alternative lacquer, acrylic and permanent marker removers which do not contain compounds detrimental to the environment and human health.

SUMMARY OF THE INVENTION

The formulation of the present disclosure is environmentally benign and effective for graffiti removal. This formulation is particularly effective for removal of marker graffiti, which is common in areas such as public restrooms, transit vehicles, bus stations, vehicular traffic control devices, and car and truck bodies. The formulation is also effective on fresh and semi-dry paint. This formulation addresses a long-felt need, considering the relative ineffectiveness of existing products and the large scope of the problem posed by graffiti.

The graffiti remover of the present disclosure is non-flammable, non-carcinogenic and has no hazardous or harmful ingredients. The graffiti remover poses no threat to human health and can be safely used in the absence of mechanical ventilation, even in a school during school hours. The graffiti remover also effectively removes gum, permanent marker, overspray and spray paint from vehicles without harming clear or gel coat. Additional uses would be apparent to one of ordinary skill in the art.

DETAILED DESCRIPTION

The present disclosure provides compositions for removing lacquer, acrylic, and permanent marker using mixtures including at least one methyl ester and propylene carbonate. In one embodiment, at least two solvents are combined in a mixture such that an effective amount of the mixture rapidly and effectively removes lacquer as provided herein.

Compositions provided herein have relatively low volatility and little or no odor, show low toxicity, are environmentally benign and biodegradable. Methods provided herein generate little or no odor, have low toxicity, and are highly effective on a wide range of surfaces.

The term "lacquer remover" as used herein refers to a composition capable of interacting with permanent marker, lacquers and acrylics such as paint or marker such that application of lacquer remover to a surface having permits removal of the offending lacquer from the surface. The term "lacquer" is not meant to be limiting, rather, it is the most common use for the remover of the present disclosure. It is understood that lacquer remover will solubilize, dissolve, weaken, loosen, or otherwise disrupt the lacquer, or other material such as gum and marker, in order to remove it from the surface.

The term "solubilize" is used generally herein to refer to the action of lacquer remover on lacquer, where the lacquer dissolves into the lacquer remover. The term "solubilized lacquer" is used generally herein to refer to the resulting mixture of lacquer and lacquer remover that can be removed from the surface. The term "removing lacquer" as used herein refers to application of lacquer remover to a surface having lacquer thereon, allowing the lacquer remover to solubilize the lacquer, and removing the resulting solubilized lacquer from the surface.

Application of the lacquer remover may be accomplished using any convenient method including but not limited to using a tissue (paper or non-cellulose tissue), a cotton ball, a sponge, a brush, or a stick to apply lacquer remover to a surface, or spraying or squeezing lacquer remover on a surface, or dipping a surface in lacquer remover.

In the application, effective amounts are generally those amounts listed as the ranges or levels of ingredients in the descriptions, which follow hereto. Unless otherwise stated, amounts listed in percentage (%) are in weight percent based on 100% of the total composition.

The time required for softening and loosening a lacquer coating varies with the percentage of solvents being used and the composition of the substance being removed.

Method of Application

The "lacquer remover" composition of the present disclosure may be applied to the target surface by a variety of means, including direct application by means of a spray, pump or aerosol dispensing means, or by other means, including the use of a carrier, or dilution system, as for example, but not limited to a wash, dip or immersion process. Regarding applications by use of a carrier, such suitable carriers include, for example, an impregnated wipe, foam, sponge, cloth, towel, tissue or paper towel or similar reasonably absorbent carrier that enables the inventive compositions to be applied by direct physical contact and transferred from the carrier to the target surface, generally during a spreading, padding, rubbing or wiping operation. Combinations of a direct application, followed by a spreading, padding, rubbing or wiping operation performed with the aid of a foam, sponge, cloth, towel, tissue or paper towel, squeegee or similar wiping implement is also suitable for applying the lacquer remover compositions of the present disclosure.

The lacquer remover composition may be also be sprayed directly onto the target surface and therefore are typically packaged in a spray dispenser. The spray dispenser can be any of the manually activated means for producing a spray of liquid droplets as is known in the art, e.g., trigger-type, pump-type, electrical spray, hydraulic nozzle, sonic nebulizer, high pressure fog nozzle, non-aerosol self-pressurized, and aerosol-type spray means. Automatic activated means can also be used herein. These types of automatic means are similar to manually activated means with the exception that the propellant is replaced by a compressor. The spray dispenser can be an aerosol dispenser. Said aerosol dispenser comprises a container which can be constructed of any of the conventional materials employed in fabricating aerosol containers. A more complete description of commercially available aerosol-spray dispensers appears in U.S. Pat. Nos. 3,436,772 and 3,600,325, both of which are fully incorporated herein by reference. Alternatively, the spray dispenser can be a self-pressurized non-aerosol container having a convoluted liner and an elastomeric sleeve. A more complete description of self-pressurized spray dispensers can be found in U.S. Pat. Nos. 4,260,110; 5,111,971 and 5,232,126, both of which are fully incorporated herein by reference. The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. Other materials can include stainless steel. A more complete disclosure of commercially available dispensing devices appears in: U.S. Pat. Nos. 4,082,223; 4,161,288; 4,274,560; 4,434,917; 4,735,347; 4,819,835; 4,895,279; and 5,303,867; all of which are fully incorporated herein by reference.

One of skill in the art would understand the term "about" is used herein to mean that a concentration of "about" a recited percentage (%) produces the desired degree of effectiveness in the compositions and methods of the present invention. One of skill in the art would further understand that the metes and bounds of "about" with respect to the concentration of any component in an embodiment can be determined by varying the concentration of one or more components (all percentages listed herein are by weight, as would be understood by one of ordinary skill in the art), determining the effectiveness of the mixture for each concentration, and determining the range of concentrations that produce mixtures with the desired degree of effectiveness in accordance with the present disclosure. The term "about" is further used to reflect the possibility that a mixture may contain trace components of other materials that do not alter the effectiveness or safety of the mixture.

It will be understood that emollients, humectants, fragrances, coloring agents, and other components may be added to or used with the compositions and methods provided herein. One of skill in the art can select additional components and determine suitable amounts and formulations such that the final composition functions with the desired degree of effectiveness to remove lacquer as provided herein.

The foregoing descriptions illustrate selected embodiments of the present invention and in light thereof various modifications will be suggested to one of skill in the art, all of which are in the spirit and purview of this invention.

FORMULATION EXAMPLES

The formulation of the present disclosure comprises a mixture of about 52-97% propylene carbonate, about 3.0-30.0% Soy Methyl Ester, and about 0.05-18.0% Ethoxylated Alcohol C9-11. The formulation of the present disclosure is generally applied at a pH of between 6.0 and 8.0.

The CAS number for Propylene Carbonate is 108-32-7. The CAS number for Soy Methyl Ester is 67784-80-9. The CAS number for Ethoxylated Alcohol C9-11 is 68439-46-3.

A first specific embodiment of the formulation of the present disclosure comprises a mixture of 65% propylene carbonate, 21.5% Soy Methyl Ester, 13.5% Ethoxylated Alcohol C9-11. The first formulation of the present disclosure is generally applied at a pH of between 6.0 and 8.0. The first specific embodiment of the formulation of the present disclosure is applied at a pH of 7.0.

A second specific embodiment of the formulation of the present disclosure comprises 95.0% propylene carbonate, about 5.0% Soy Methyl Ester, 0.1% Ethoxylated Alcohol C9-11. The second specific embodiment of the formulation of the present disclosure is applied at a pH of 7.0.

Additional embodiments of this formulation can be selected from a group where CAS 68439-46-3 is substituted with a compound selected from a group of CAS 68002-97-1, CAS 34398-01-1, CAS 68131-39-5, or CAS 66455-14-9, or any combination of CAS 68439-46-3, CAS 68002-97-1, CAS 34398-01-1, CAS 68131-39-5, or CAS 66455-14-9. The carbon chain length of CAS 68439-46-3 CAS 68002-97-1, CAS 34398-01-1, CAS 68131-39-5, or CAS 66455-14-9 may be varied to achieve similar chemical activity.

The formulations of the present disclosure may further comprise a chelating agent. A shine polymer may further be added for those applications requiring a shined surface following cleaning. Optional compositions further contain dyes and/or fragrances.

What is claimed is:

1. A lacquer remover comprising:

a) 58.0-66.0 wt. % of a propylene carbonate;

b) 16.0-24.0 wt. % of a soy methyl ester;

c) 3.0-18.0 wt. % of a mixture of two ethoxylated alcohols, wherein each ethoxylated alcohol has an alkyl chain length of from 9-11 carbon atoms and a degree of ethoxylation of from 5.0 to 9.0 moles of ethylene oxide on average; and wherein the lacquer remover is environmentally benign and non-toxic.

2. A lacquer remover comprising:

a) about 65 wt. % propylene carbonate;

b) about 21.5 wt. % soy methyl ester;

c) 13.5 wt. % of a mixture of two ethoxylated alcohols, wherein each ethoxylated alcohol has an alkyl chain length of from 9-11 carbon atoms and a degree of ethoxylation of from 5.0 to 9.0 moles of ethylene oxide on average; and wherein the lacquer remover is environmentally benign and non-toxic.

3. A lacquer remover comprising:

a) 58.0-66.0 wt. % of a propylene carbonate;

b) 16.0-24.0 wt. % of a soy methyl ester;

c) 12.0-18.0 wt. % of a mixture of two ethoxylated alcohols, wherein each ethoxylated alcohol has an alkyl chain length of from 9-11 carbon atoms and a degree of ethoxylation of from 5.0 to 9.0 moles of ethylene oxide on average.

* * * * *